(12) United States Patent
Hussan (10) Patent No.: US 8,103,454 B2
(45) Date of Patent: Jan. 24, 2012

(54) SPATIALLY HETEROGENEOUS STOCHASTIC PETRI-NET MODELING

(75) Inventor: Jagir Razak Jainul Abdeen Hussan, Tamil Nadu (IN)

(73) Assignee: International Business Machines Corporation, Armonk, NY (US)

( * ) Notice: Subject to any disclaimer, the term of this patent is extended or adjusted under 35 U.S.C. 154(b) by 1912 days.

(21) Appl. No.: 11/215,754

(22) Filed: Aug. 30, 2005

(65) Prior Publication Data

US 2007/0050147 A1 Mar. 1, 2007

(51) Int. Cl.
G01N 33/48 (2006.01)
G01N 33/50 (2006.01)
G06F 17/50 (2006.01)
G01F 7/60 (2006.01)

(52) U.S. Cl. .................................. 702/19; 703/1; 703/2
(58) Field of Classification Search .................. None
See application file for complete search history.

(56) References Cited

U.S. PATENT DOCUMENTS

| | | | |
|---|---|---|---|
| 3,156,968 A | 11/1964 | White, Jr. | |
| 3,156,986 A | 11/1964 | White, Jr. | |
| 5,424,963 A | 6/1995 | Turner et al. | |
| 5,590,051 A | 12/1996 | Yokozawa | |
| 5,745,385 A | 4/1998 | Hinsberg, III et al. | |
| 5,930,154 A | 7/1999 | Thalhammer-Reyero | |
| 5,980,096 A | 11/1999 | Thalhammer-Reyero | |
| 6,508,652 B1 | 1/2003 | Kestyn | |
| 6,708,141 B1 | 3/2004 | Schaff et al. | |
| 6,710,711 B2 | 3/2004 | Berry | |
| 6,785,665 B2 | 8/2004 | Sun | |
| 2004/0167763 A1* | 8/2004 | Liebman | 703/11 |

FOREIGN PATENT DOCUMENTS

WO WO-02-099569 A2 12/2002

OTHER PUBLICATIONS

Finkel et al., Quad Trees A Data Structure for Retrieval on Composite Keys, 1974, Acta Informatica, vol. 4, pp. 1-9.*
Goss et al., Quantitative modeling of stochastic systems in molecular biology by using stochastic Petri nets, Proc. Natl. Acad. Sci. USA, vol. 95, pp. 6750-6755, Jun. 1998.

\* cited by examiner

*Primary Examiner* — Jason Sims
(74) *Attorney, Agent, or Firm* — Schmeiser, Olsen & Watts; John Pivnichny

(57) ABSTRACT

Modeling of biochemical reactions of a system is accomplished using spatially heterogeneous stochastic Petri-net modeling. The biochemical reactions of the system to be modeled are defined. A spatial decomposition of the system is defined by defining regions of a space in which the system is to be modeled and by assigning each biochemical reaction to a region, such that the system is spatially heterogeneous. Relationships for inter-region movement of reactants of the biochemical reactions are defined as flux, advection, convection, and/or diffusion-based molecular movements. The system of the biochemical reactions is then modeled by modeling the biochemical reactions of each region as a spatially homogenous stochastic Petri-net and by modeling the inter-region movement of the reactants based on the relationships as defined.

11 Claims, 6 Drawing Sheets

SPATIALLY HETEROGENEOUS STOCHASTIC PETRI-NET MODELING

FIELD OF THE INVENTION

The present invention relates generally to stochastic Petri-net modeling, and more specific to modeling spatially heterogeneous systems using stochastic Petri-net modeling.

BACKGROUND OF THE INVENTION

To understand the molecular logic of a cell, methods of modeling and simulation are important. The primary motivation for using computer-aided study mechanisms is that observing biochemical systems and conducting experiments on them is difficult. Yet, such observation and experimentation can be necessary to improve health care. For example, the study of gene regulatory and metabolic networks plays an important role in the detection of genetic or metabolic defects, as well as in therapeutic drug research. Genetic and metabolic defects often lead to diseases like high blood pressure, Alzheimer's, cancer, and diabetes. Biochemical models can be used to integrate detailed biochemical data, and to help understand the behavior of complex systems of molecular interactions. Building such biochemical models has remained an art and an arduous task.

Many processes in molecular biology, as well as other biochemical systems, demonstrate a stochastic nature. Such biological phenomena necessitate the use of stochastic models. The primary difference between deterministic and stochastic models is that in a deterministic model an initial condition results in one, and only one, final outcome, whereas in a stochastic model distinct final outcomes can arise from identical initial conditions. Therefore, the theoretical understanding of molecular and developmental biology using computational systems has to account for variations caused by the stochastic interactions of molecules and other reactants, as well as the large variety of these molecules and the complex feedback loops characterizing biochemical systems. Traditional mathematical tools are not well suited to modeling such dynamic behavior.

One type of mathematical formalism that has been applied to biochemical systems is the Petri-net. The Petri-net formalism is a graphically oriented language of design, specification, simulation, and verification of systems. It offers methods to represent the structure of a discrete-event system, to simulate the system's behavior, and to draw certain types of general conclusions regarding the properties of the system. Simple Petri-net models, however, do not provide features that can capture quantitative aspects of stochastic biochemical systems.

However, the reference P J E Goss and Peccoud, "Quantitative modeling of stochastic systems in molecular biology using stochastic Petri-nets," in Proceedings of the National Academy of Sciences, USA, vol. 95, pp. 6750-6755 (June 1998) [hereinafter Goss and Peccoud], describes an extended Petri-net formalism having features that allow for the modeling of stochastic biochemical systems. Such augmented Petri-net frameworks may be referred to as spatially homogenous stochastic Petri-net frameworks, and have been successfully applied to the modeling and simulation of many complex biological and other biochemical systems.

A significant drawback of the spatially homogenous stochastic Petri-net framework described in [Goss and Peccoud] is its inability to represent space heterogeneously, and hence its inability to model effects resulting from non-uniform spatial distributions of interacting molecules and other reactants. In other words, current Petri-net frameworks are unable to model systems existing within spatially heterogeneous spaces, in which biochemical reactants are non-uniformly spatially distributed. For this and other reasons, therefore, there is a need for the present invention.

SUMMARY OF THE INVENTION

The present invention relates to spatially heterogeneous systems modeling using stochastic Petri-net. A method of the present invention defines one or more biochemical reactions of a system to be modeled. Each biochemical reaction has one or more reactants, such as molecules. The method defines a spatial decomposition of the system, by defining regions of a space in which the system is to be modeled, and by assigning the biochemical reactions to all the regions, and by assigning the molecular distribution of the reactants of the reactions among the regions, such that the regions are initially populated within the regions in accordance with this distribution. The result is that the system is spatially heterogeneous. The method further defines relationships for inter-region movement of the reactants of the biochemical reaction. These relationships may be flux, advection, convection, and/or diffusion-based molecular movement. The method models the system of the biochemical reactions by modeling the biochemical reactions of each region as a spatially homogenous stochastic Petri-net, and by modeling the inter-region movement of the reactants based on the relationships that have been defined, such as based on flux, advection, convection, and/or diffusion-based molecular movement.

A system of the present invention includes one or more processors, one or more computer-readable media, and a computer program. The computer-readable media may each be a volatile or non-volatile medium, as well as a magnetic, optical, and/or semiconductor medium. The media store data representing one or more biochemical reactions and a number of regions of a space. Each biochemical reaction is assigned to all the regions, but the molecular distribution of the various species present in the region is varied such that the biochemical reactions are spatially heterogeneous. The computer program is executed by the processors to model the biochemical reactions of each region as a spatially homogenous stochastic Petri-net. The computer-readable media may further store data representing relationships corresponding to potential inter-region movement of reactants of the biochemical reactions, such that the computer program may further model inter-region movement of the reactants based on these relationships, which may be flux, advection, convection, and/or diffusion-based molecular movement.

An article of manufacture of the present invention includes a computer-readable medium, and means in the medium. The medium may be a volatile or a non-volatile medium, as well as a magnetic, optical, and/or semiconductor medium, or a modulated carrier signal. The means is for modeling a system of one or more biochemical reactions as a spatially heterogeneous stochastic Petri-net. The means may model each biochemical reaction as a spatially homogeneous stochastic Petri-net within a region of a space into which the system has been spatially heterogeneously decomposed. The means may further model inter-region movement of reactants of the biochemical reactions as flux, advection, convection, and/or diffusion-based molecular movement.

Embodiments of the invention provide for advantages over the prior art. Unlike the spatially homogenous stochastic Petri-net modeling described in [Goss and Peccoud], the present invention provides for modeling spatially heterogeneous systems using stochastic Petri-nets. The net result is that more accurate modeling of biochemical systems can be achieved, since the spatially heterogeneous nature of such systems is captured within the modeling.

In particular, the present invention provides a methodology by which as spatially homogenous stochastic Petri-nets, can be used to model spatially heterogeneous systems. A system of biochemical reactions is compartmentalized by representing and treating each compartment of the system, such as each region or orthant, as a homogeneous well-mixed system, and using the spatially homogenous stochastic Petri-net formalism to represent the biochemical reactions within the region. The movement of reactants, such as molecules, across compartments is represented as flux, advection, convection, and/or diffusion-based molecular movement.

Still other advantages, aspects, and embodiments of the invention will become apparent by reading the detailed description that follows, and by referring to the accompanying drawings.

BRIEF DESCRIPTION OF THE DRAWINGS

The drawings referenced herein form a part of the specification. Features shown in the drawing are meant as illustrative of only some embodiments of the invention, and not of all embodiments of the invention, unless otherwise explicitly indicated, and implications to the contrary are otherwise not to be made.

DETAILED DESCRIPTION OF THE DRAWINGS

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

Technical Background: Spatially Homogenous Stochastic Petri-Nets

Figure 1:
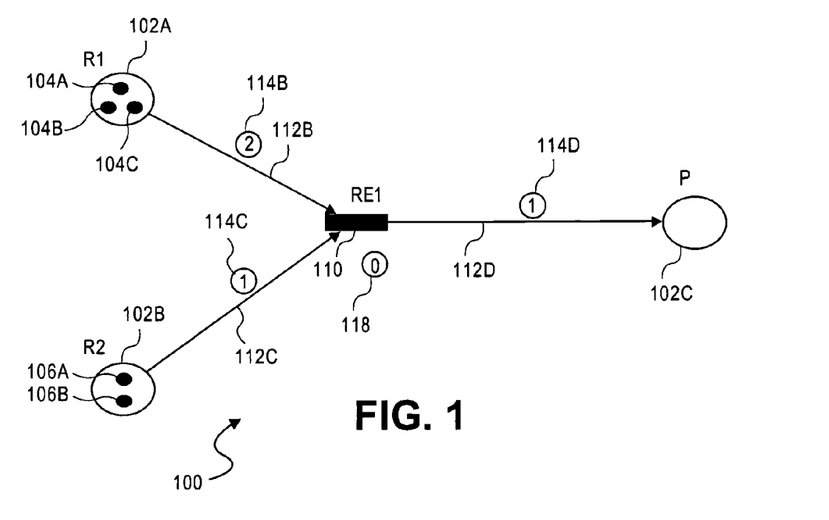
FIG. 1 is a diagram of an example and representative biochemical system modeled as a spatially homogenous stochastic Petri-net, in conjunction with which embodiments of the invention may be practiced.

FIG. 1 shows a spatially homogenous stochastic Petri-net representation of an example and representative biochemical system 100, in conjunction with which embodiments of the invention may be practiced. The various elements of the biochemical system 100 are represented as different elements of the stochastic Petri-net. There are places 102A, 102B, and 102C, collectively referred to as the places 102. Each place of the stochastic Petri-net represents a molecular species. Each place can have zero or more tokens located thereat, where each token represents an individual molecule or other reactant of the molecular species that the place represents. For instance, in FIG. 1 there are tokens 104A, 104B, and 104C, collectively referred to the tokens 104, located at the place 102A, and there are tokens 106A and 106B, collectively referred to as the tokens 106, located at the place 102B. There are no tokens located at the place 102C.

There is also in FIG. 1 a transition 110. A transition of the stochastic Petri-net represents a reaction. A reaction is the creation, generation, or transformation of one or more molecules or other reactants from one or more existing molecules or other reactants. For example, the transition 110 represents a biochemical reaction in which the reactants denoted by R1 are combined with the reactants denoted by R2 to result in the product denoted by P.

The places 102 and the transition 110 are linked by input/output functions 112B, 112C, and 112D, collectively referred to as the input/output functions 112. An input/output function implements the stoichiometric constraints governing the reactions being modeled. Each of the input/output functions 112 is represented as a directed arc. The functions 112 have corresponding weights 114B, 114C, and 114D, collectively referred to as the weights 114. The weights 114 indicate the stoichiometric requirements for and outputs of the occurrence of their corresponding transitions.

For example, the input/output function 112B has a weight 114B of two, and the input/output function 112C has a weight 114C of one, indicating that two of the tokens 104 of the place 102A and one of the tokens 106 of the place 102B are consumed in the reaction represented by the transition 110. Furthermore, the input/output function 112D has a weight 114D of one, indicating that the reaction represented by the transition 110 results in one token being generated within the place 102C.

The transition 110 further has a label 118. A label indicates the number of time steps that are to occur between successive firings of the transition to which the label corresponds. For example, the transition 110 has a label 118 of zero, indicating that the reaction represented by the transition 110 is instantaneous, and can occur so long as there are sufficient tokens as required by the weights 114B and 114C of the input/output functions 112B and 112C leading to the transition 110.

The transition 110 is said to be enabled when all of its input places 102A and 102B have a number of tokens greater than or equal to the weights 114B and 114C of the corresponding input/output functions 112B and 112C. Enabled transitions are able to fire, and each firing event represents the occurrence of the biochemical reaction represented by a corresponding transition. The decision as to whether a transition fires or not is probabilistic, or stochastic or random, and is further governed by the label 118 of the transition 110 as has been described.

As has been noted, each of the places 102 is able to hold one or more of the tokens 104 and 106. The number of tokens in a place is referred to as the marking of the place. A vector representing the tokens in each place at a given moment t is referred as the global marking Mt of the biochemical system 100. For example, the biochemical system 100 has a global marking M={3, 2, 0} at the time depicted in FIG. 1. This means that there are three tokens 104 within the place 102A, two tokens 106 within the place 102B, and no tokens within the place 102C.

Thus, the stochastic Petri-net representation of the system 100 of FIG. 1 has three places, also denoted as the places R1, R2, and P. The place R1 represents a first reactant, the place R2 represents a second reactant, and the place P represents the product of the first and the second reactants resulting from the biochemical reaction represented by the transition also denoted by Re1. There is one transition: the transition denoted by Re1 that represents a reaction involving the first and the second reactants, and producing the product thereof The input functions for the reaction represented by the transition denoted by Re1 determine the stoichiometric requirements for the reaction. This reaction is:

$2R_1 + R_2 \rightarrow P.$

Because the label 118 of the transition 110 is zero, the reaction represented by the transition denoted by Re1 is instantaneous, such that if possible the transaction Re1 fires each time step and consumes one token each from the places R1 and R2, producing a token in P1.

Figure 2:
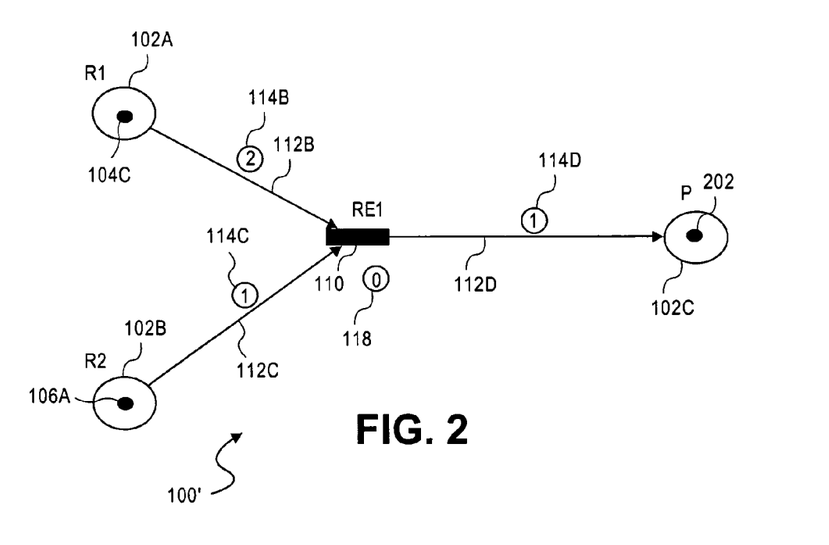
FIG. 2 is a diagram of the biochemical system of FIG. 1 after the spatially homogenous stochastic Petri-net model has been run, in conjunction with which embodiments of the invention may be practiced.

FIG. 2 shows an example of the spatially homogenous stochastic Petri-net representation of the example and representative biochemical system 100 of FIG. 1 after one or more time steps. The system 100 of FIG. 1 is indicated as the system 100' in FIG. 2 to differentiate the different points in time that the system 100 is depicted in FIG. 1 as compared to FIG. 2. In FIG. 2, the transition 110 representing a reaction and denoted by Re1 has fired.

As a result, there is one token within the place 102A also denoted by R1. This is because two of the tokens were consumed by the reaction of the transition 110, as required by the weight 114B of the input/output function 112B. Furthermore, there is just one token 106A within the place 102B also denoted by R2. This is because the other token 106B was consumed by the reaction of the transition 110, as required by the weight 114C of the input/output function 112C. Finally, there is one token 202 within the place 102C denoted by P. This is because the reaction of the transition 110 resulted in the generation of the token 202 at the place 102C, as indicated by the weight 114D of the input/output function 112D.

It is noted that the biochemical system 100 modeled in FIGS. 1 and 2 using spatially homogenous Petri-nets is stochastic. This means that while the transition 110 has fired in the example of FIG. 2, in a different running of the system 100, with the same initial conditions as in FIG. 1, the transition 110 may not fire, even though the transition 110 is enabled and thus capable of firing. That is, the stochastic, or random or probabilistic, nature of the system 100 means that the final outcome of modeling the system 100 may be different even with the same initial conditions of the system 100.

Furthermore, the biochemical system 100 is modeled in FIGS. 1 and 2 using stochastic Petri-nets that are spatially homogenous. This means that all of the molecules or other reactants corresponding to a given species can be represented by one of the single places 102, which occurs only where the system 100 is well mixed, and spatially uniform. However, in many types of systems, this spatial homogeneity assumption is invalid, as molecules and other reactants are distributed unequally or non-uniformly within a given space, such that the reactions in which they participate can vary greatly.

Figure 3:
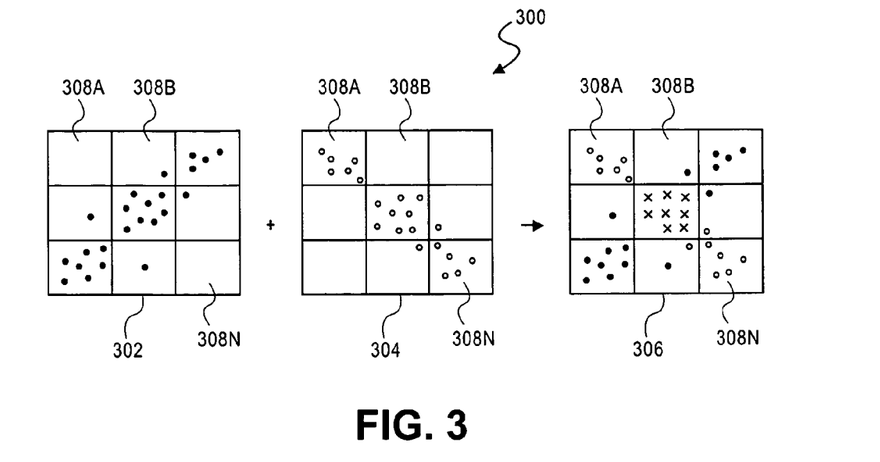
FIG. 3 is a diagram of the example modeling of a representative biochemical system, taking into account the spatially heterogeneous nature of the system, according to an embodiment of the invention.
Figure 4:
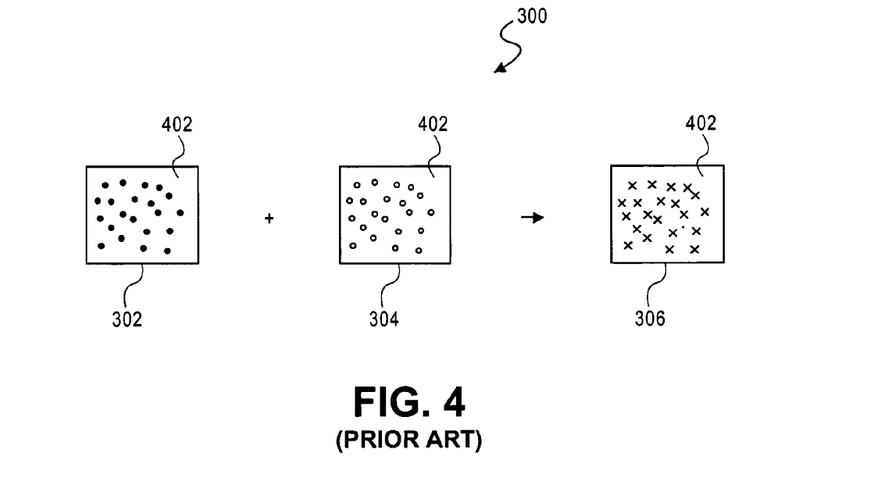
FIG. 4 is a diagram of the example modeling of the representative biochemical system of FIG. 3, in which the system is instead presumed to be spatially homogeneous, to demonstrate the advantages of the embodiment of FIG. 3 over the prior art.

FIGS. 3 and 4 show how presuming that a spatially heterogeneous biochemical system 300 is spatially homogenous can affect the modeling of the system 300. FIG. 3 shows the results of modeling a spatially heterogeneous biochemical system 300 in accordance with an embodiment of the invention, whereas FIG. 4 shows the results of modeling the system 300 where the system 300 is presumed to be spatially homogenous, such that the spatially heterogeneous nature of the system 300 is ignored. In FIG. 3, in other words, modeling of the biochemical system 300 is accomplished while preserving the spatially heterogeneous, or spatially non-uniform, nature of the system 300. By comparison, in FIG. 4, modeling of the biochemical system 300 is accomplished while ignoring the spatial heterogeneous, or spatially non-uniform, nature of the system 300.

First referring to FIG. 3, there are two sets of reactants 302 and 304 within the biochemical system 300. The reactants 302 are denoted as solid circles and the reactants 304 are denoted as hollow circles for illustrative clarity. The reactants 302 are heterogeneously, or non-uniformly, distributed over a number of spatial regions 308A, 308B, . . . , 308N, collectively referred to as the spatial regions 308, as shown in FIG. 3, as are the reactants 304. The reaction of the reactants 302 and 304 results in the set of products 306, which are denoted as small X's in FIG. 3 for illustrative clarity.

The products 306 in FIG. 3 are concentrated in the middle spatial region, because this is substantially the only region in which there is substantial overlap between the reactants 302 and the reactants 304. As a result, even after the products 306 have been generated, there are significant numbers of both the reactants 302 and the reactants 304. For instance, because there are only reactants 302 in the upper-right and the lower-left regions, and none of the reactants 304 in these regions, the reactants 302 in these regions remain even after the reactants 302 and 304 have reacted with one another to generate the products 306 in the central region. Similarly, because there are only reactants 304 in the upper-left and lower-right regions, and none of the reactants 302 in these regions, the reactants 304 in these regions remain even after the reactants 302 and 304 have reacted with one another to generate the products 306 in the central region.

Referring next to FIG. 4, there are still two sets of reactants 302 and 304 within the biochemical system 300, denoted as solid circles and hollow circles, respectively. However, it is presumed that the reactants 302 are homogenously, or uniformly, distributed over a single spatial region 402, and similarly it is presumed that the reactants 304 are homogenously, or uniformly, distributed over the same spatial region 402. The reaction of the reactants 302 and 304 again results in the set of the products 306, which are denoted as small X's.

However, in FIG. 4 all of the reactants 302 and 304 have been consumed to generate the products 306. This is because of the spatial homogeneity assumption. That is, since there are sufficient numbers of both the reactants 302 and 304 in FIG. 4, all possible reactions between these two reactants 302 and 304 resulting in the products 306 occur, because it is presumed that the reactants 302 and 304 are well mixed and thus spatially homogeneous within the spatial region 402. None of the reactants 302 and 304 thus remain upon generation of the products 306 in FIG. 4, in contradistinction to FIG.

3. Comparison of FIGS. 3 and 4 therefore shows how assuming spatial homogeneity can significantly affect modeling of a biochemical system.

The modeling of the biochemical system 300 can be accomplished as in FIG. 3 by performing an embodiment of the invention, such as that described in subsequent sections of the detailed description. The modeling of the system 300 as accomplished in FIG. 3 thus depicts the advantages of the invention as compared to the prior art. Embodiments of the invention take into account the heterogeneously spatial nature of biochemical systems during modeling, as depicted in FIG. 3, whereas prior art approaches like that of [Goss and Peccoud] do not, as depicted in FIG. 4, and instead assume spatial homogeneity even where the system in question is spatially heterogeneous.

Spatially Heterogeneous Stochastic Petri-Net Modeling

Figure 5:
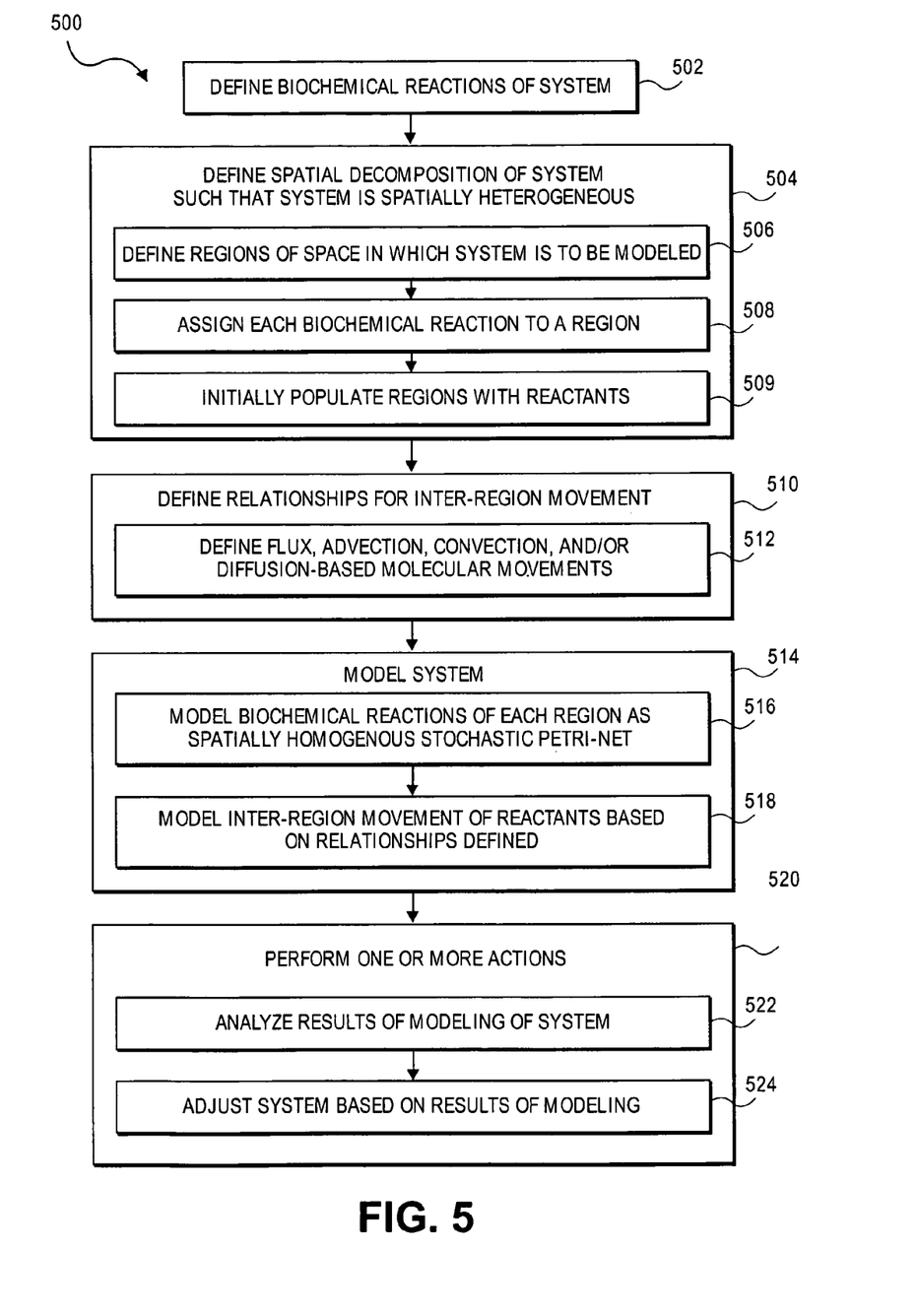
FIG. 5 is a flowchart of a method for heterogeneously spatial stochastic Petri-net modeling of a biochemical system, according to an embodiment of the invention.

FIG. 5 shows a method 500 for spatially heterogeneous stochastic Petri-net modeling of a biochemical system, according to an embodiment of the invention. The method 500 leverages the spatially homogenous stochastic Petri-net modeling that has been described in relation to FIGS. 1 and 2. As an overview, the biochemical reactions of a biochemical system are assigned to different regions of a space to take into account the spatial heterogeneity of the biochemical system within the space. Thereafter, the biochemical reactions assigned to each region are modeled as separate spatially homogenous stochastic Petri-nets, with interactions between the regions modeled using advection, convection, and/or diffusion-based molecular movement.

Figure 6:
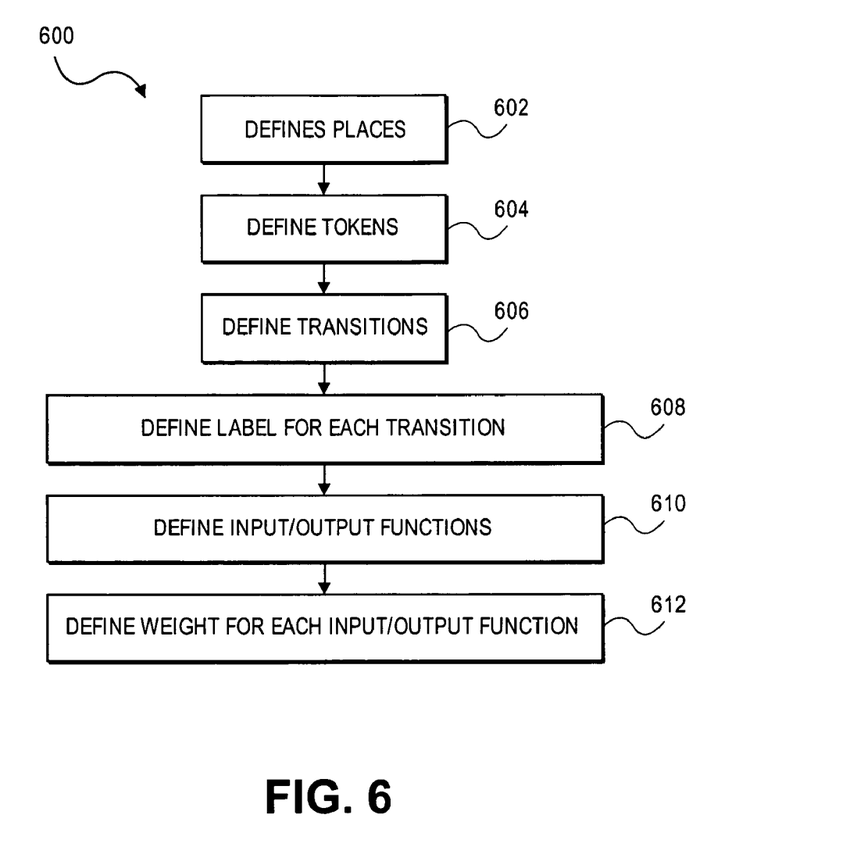
FIG. 6 is a flowchart of a method to define a biochemical reaction as a stochastic Petri-net model, according to an embodiment of the invention.

The method 500 begins by defining the biochemical reactions of the biochemical system (502). Definition of the biochemical reactions of the biochemical system can in one embodiment be accomplished by performing the method 600 of FIG. 6 for each biochemical reaction. The method 600 is specifically for defining a stochastic Petri-net model for a biochemical reaction, such as a spatially homogenous stochastic Petri-net model. Referring now to FIG. 6, the number of places of a stochastic Petri-net for a biochemical reaction is defined (602). The tokens that initially populate the places are also defined (604). Each token corresponds to a reactant, such as a molecule, within the biochemical reaction, and is initially located in one of the places of the stochastic Petri-net that have been defined.

The method 600 next defines the transitions of the stochastic Petri-net for the biochemical reaction (606). Each transition corresponds to a reaction, as has been described in relation to FIG. 1. The method 600 further defines a label for each transition (608). Each label corresponds to the number of time steps that are to occur between successive firings of its corresponding transition. A label of zero indicates that a number of such firings can occur instantaneously, insofar as there are sufficient tokens to be input to and consumed by the corresponding transition.

One or more input/output functions of the stochastic Petri-net are then defined (608). Each input/output function links an input place or transition to an output place or transition, as a directed arc, as has been described in relation to FIG. 1. Furthermore, a weight is defined for each input/output function (610). The weight of an input/output function corresponds to the number of tokens required for the input/output function to occur.

Each transition thus has one or more input/output functions leading from a place to the transition. The transition is enabled when each place leading to the transition via an input/output function has a number of tokens located therein greater than or equal to the weight specified by the input/output function in question. Furthermore, at least one of the places can be an output place. An output place has one or more input/output functions leading to the output place, and leading from another place or a transition. The occurrence of each input/output function of the output place results in transfer of tokens from the other place or the transition leading from the input/output function to the output place. In FIG. 1, the place 102 is an output place.

Referring back to FIG. 5, a spatial decomposition of the biochemical system is next defined, such that the system is spatially heterogeneous (504). Definition of the spatial decomposition of the system ensures that the spatial heterogeneity of the biochemical system being modeled is taken into account. That is, the biochemical system is decomposed over a space, such that the system is spatially heterogeneous. The degree of precision to which the biochemical system is spatially decomposed corresponds to the desired accuracy of the modeling of the system. A complex spatial decomposition, for instance, likely results in greater accuracy of the resulting modeling of the biochemical system than does a relatively simple spatial decomposition.

In one embodiment, spatial decomposition of the biochemical system is accomplished as follows. First, the space within which the biochemical system is to be modeled is divided into a number of regions, or compartments, such as a number of orthants (506). Each biochemical reaction defined in 502 is then assigned to one of these regions (508). A given region may encompass zero, one, or more than one of the molecular species involved in the biochemical reactions of the system, based on the molecules spatial distribution and the position of the region in that space. Finally, the regions of the system are initially populated with reactants (509), according to a desired initial molecular distribution.

Figure 7:
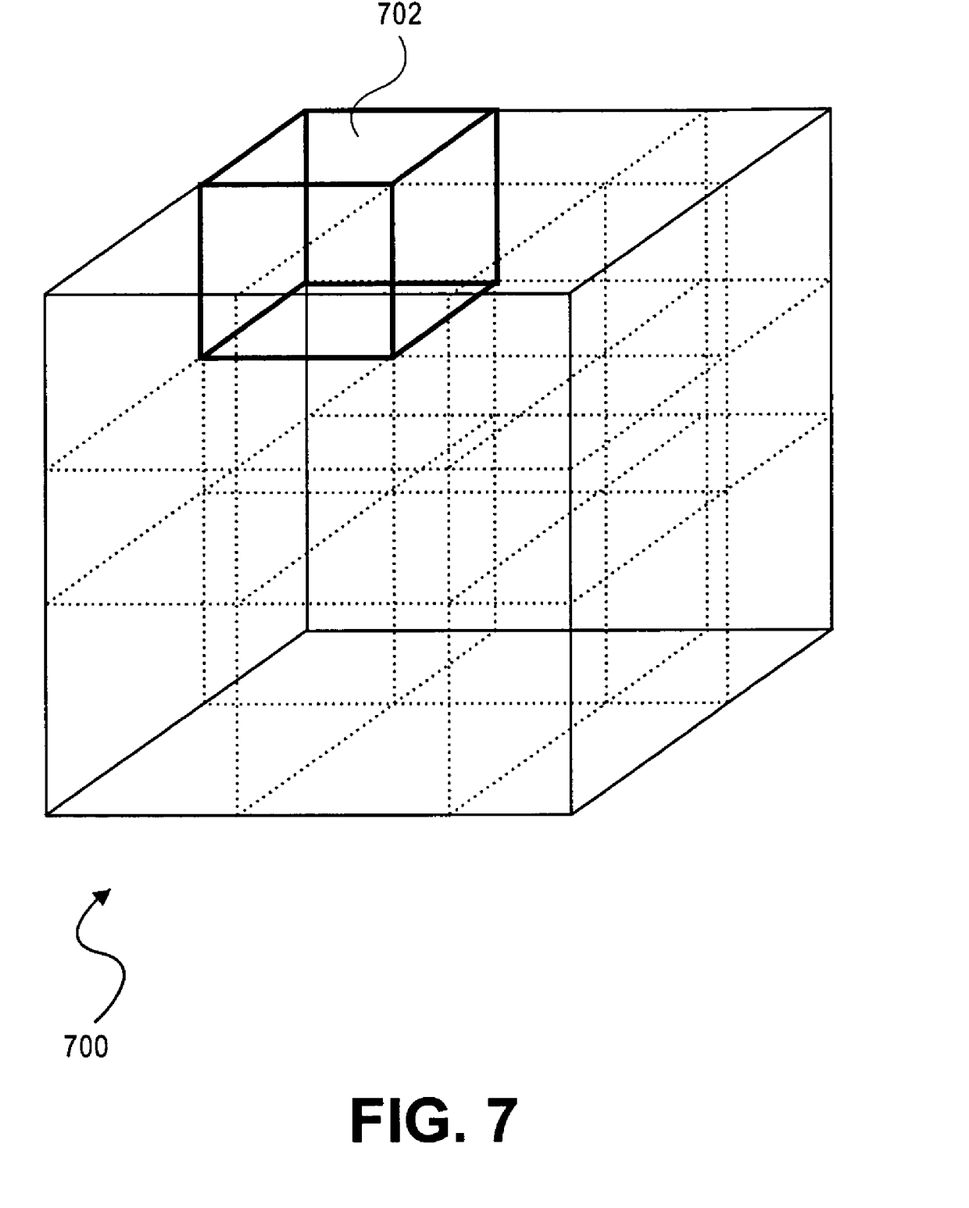
FIG. 7 is a diagram depicting spatial decomposition of a three-dimensional cubic space into a number of three-dimensional spatial regions, or orthants, according to an embodiment of the invention.

FIG. 7 shows an example spatial decomposition of a biochemical system, according to an embodiment of the invention, which may be performed as the spatial decomposition in 504 of the method 500 of FIG. 5. Referring now to FIG. 7, there is a cubic three-dimensional space 700 within which the biochemical system is to be modeled. This space 700 is divided into a number of three-dimensional regions, or orthants, such as the region or orthant 702, in 506 of the method 500 of FIG. 5. Each orthant is a unique three-dimensional sub-space of the three-dimensional space 700. In 508 of the method 500, then, each biochemical reaction is assigned to one of these regions.

As can be appreciated by those of ordinary skill within the art, the spatial decompositions of the biochemical system depicted in FIG. is just one example of the kinds of spatial decompositions that can be performed in 504 of the method 500 of FIG. 5. In other embodiments of the invention, other types of spatial decompositions may be employed. That is, embodiments of the invention are not limited to decomposition of a cubic space into orthants, as in FIG. 7.

Referring back to FIG. 5, the method 500 next defines relationships for inter-region movement of reactants among the regions into which the system has been spatially decomposed in 504 (510). Relationships among the regions can include flux, advection, convection, and/or diffusion-based molecular movement for inter-region movement of reactants of the biochemical reactions of the system (512), such as molecules. Other types of relationships may also be defined for such inter-region movement.

Referring back to FIG. 5, the method 500 next actually models the biochemical system in question (514). The biochemical reactions of each region as have been defined are modeled as spatially homogenous stochastic Petri-nets (516), as has been described, for instance, in relation to FIGS. 1 and 2. Inter-region movement of the reactants of these biochemical reactions are based on the input physical effects that are present in the system and the physical laws that determine their motion, which are denoted herein as relationships for inter-region movement (518). In other words, the biochemical reactions of each region are run as spatially homogenous stochastic Petri-nets, with the biochemical reactions of the regions interacting with one another via the inter-region movement of their reactants.

For example, the initial system is modeled as a number of discrete homogenous Petri-nets, which are populated by reactants in accordance with an initial molecular distribution. In each time step, each of the Petri-nets within the regions is separately executed in a homogenous manner, such that reactants are consumed, and products created, in accordance with the biochemical reactions of the Petri-nets. However, between time steps, inter-region movement of reactants (i.e., molecules) occurs in accordance with relationships that have been defined, such as flux, advection, convection, and/or diffusion-based molecular movement. That is, based on a given inter-region movement model that has been selected, reactants move among the regions. Therefore, the modeling of 514, 516, and 518 is a process in which the Petri-nets are individually run, then inter-region molecular movement occurs, the Petri-nets are again individually run, inter-region molecular movement again occurs, and so on.

Heterogeneously spatial stochastic Petri-net modeling is thus accomplished by leveraging spatially homogenous stochastic Petri-nets. Each biochemical reaction is modeled as a spatially homogenous stochastic Petri-net within its given region, and therefore can use the spatially homogenous stochastic Petri-net methodology that has been described in relation to FIGS. 1 and 2. Inter-region movement is modeled as flux, advection, convection, and/or diffusion-based molecular movement.

Once the biochemical system has been modeled—that is, once the modeling simulation has run as long as desired—one or more actions may be performed on the basis of that modeling (520). For instance, the results of the modeling of the biochemical system may be analyzed (522), such as by a scientist, to learn new insights into the functioning of the system. As another example, the biochemical system may itself be adjusted, modified, or manipulated based on the results of the modeling (524). For instance, drug development may entail adjusting the system to correspond to the effects of the revised formulation of a new drug, to determine if the revised formulation has better results or efficacy than an earlier formulation of the drug did.

Computerized System and Conclusion

Figure 8:
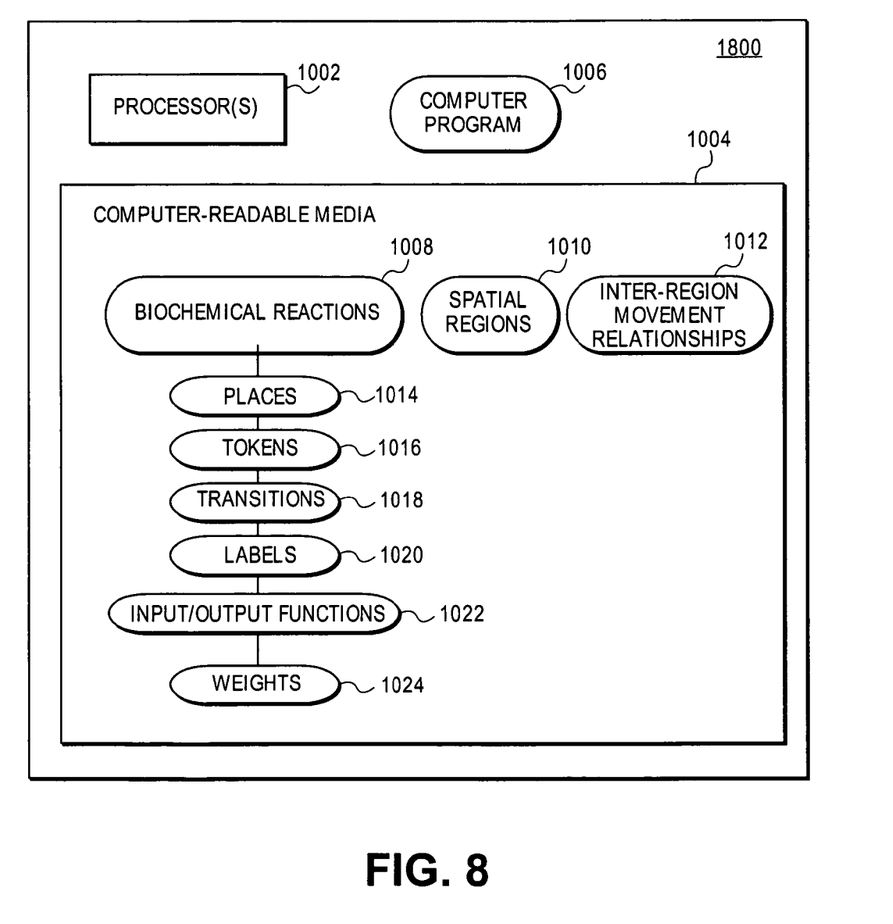
FIG. 8 is a diagram of a rudimentary computerized system for heterogeneously spatial stochastic Petri-net modeling of a biochemical system, according to an embodiment of the invention.

FIG. 8 shows a rudimentary computerized system 1800 for heterogeneously spatial stochastic Petri-net modeling of a biochemical system, according to an embodiment of the invention. As depicted in FIG. 8, the system 1800 includes one or more processors 1002, one or more computer-readable media 1004, and a computer program 1006. As can be appreciated by those of ordinary skill within the art, the system 1800 can, and typically will, include other components, in addition to and/or in lieu of those depicted in FIG. 8.

The computer-readable media 1004 may each be a volatile or non-volatile medium, as well as a magnetic, optical, and/or semiconductor medium. The media 1004 store data representing the biochemical reactions 1008 of a biochemical system that have been described, the spatial regions 1010 into which the biochemical system has heterogeneously spatially decomposed as has been described, and one or inter-region movement relationships 1012 corresponding to potential inter-region movement of reactants of the biochemical reactions 1008 as has also been described. Furthermore, the media 1004 store data representing the following for each of the biochemical reactions 1008: places 1014 of a stochastic Petri-net for the biochemical reaction; tokens 1016 for the biochemical reaction; transitions 1018 of the stochastic Petri-net; labels 1020 for the transitions 1018; input/output functions 1022 of the stochastic Petri-net; and, weights 1024 for the input/output functions 1022. Each of these data that the media 1004 store for each of the biochemical reactions 1008 is as has been described in previous sections of the detailed description.

The computer program 1006 is executed by the processors 1002, such as from the computer-readable media 1004 on which the computer program 1006 may be stored. The computer program 1006 may be made up of one or more computer program parts, sections, objects, routines, and subroutines, among other types of computer program components, as can be appreciated by those of ordinary skill within the art. The computer program 1006 further may itself be made up of more than one computer program. The computer program 1006 models the biochemical reactions 1008 of the biochemical system using a heterogeneously spatial stochastic Petri-net approach, as has been described in previous sections of the detailed description. That is, the computer program 1006 models the biochemical reactions of each region as a spatially homogenous stochastic Petri-net, and further models inter-region movement of reactants based on relationships such as flux, advection, convection, and/or diffusion, as has been described.

It is noted that, although specific embodiments have been illustrated and described herein, it will be appreciated by those of ordinary skill in the art that any arrangement calculated to achieve the same purpose may be substituted for the specific embodiments shown. For example, the types of biochemical systems that can be modeled using the spatially heterogeneous stochastic Petri-net approach described herein are not limited by embodiments of the invention. Such biochemical systems can be as diverse as the Hox gene system, for instance, which has a role in hindbrain development, as well as other biomolecular systems, and other types of biochemical systems, as can be appreciated by those of ordinary skill within the art. The terminology biochemical system is inclusive of any such type of biomolecular system. This application is thus intended to cover any adaptations or variations of embodiments of the present invention. Therefore, it is manifestly intended that this invention be limited only by the claims and equivalents thereof.

What is claimed is:

1. A method, comprising:
defining a biochemical reaction of a system, said biochemical reaction occurring between at least two reactants to form a product, said system comprising a space in which each reactant of the at least two reactants is non-uniformly spatially distributed;
defining a spatial decomposition of the space by subdividing the space into a plurality of regions, wherein each region of the plurality of regions is a unique three-dimensional sub-space of a three-dimensional space;
defining relationships for inter-region movement of the at least two reactants between different regions of the plurality of regions, wherein defining relationships for inter-region movement of the at least two reactants is selected from the group consisting of defining flux-based molecular movement, defining advection-based molecular movement, defining convection-based molecular movement, defining diffusion-based movement, and combinations thereof;

modeling the biochemical reaction in each region as a spatially homogenous stochastic Petri-net;

modeling the inter-region movement of the at least two reactants between said different regions based on the defined relationships;

determining, from said modeling the biochemical reaction in each region and said modeling the inter-region movement of the at least two reactants between said different regions, an identification of the product of the biochemical reaction in each region; and storing the identification of the product of the biochemical reaction in each region in a computer readable medium, wherein said modeling the biochemical reaction comprises modeling the biochemical reaction as occurring in a sequence of time steps, wherein said modeling the biochemical reaction in each region as a spatially homogenous stochastic Petri-net is performed in each time step, and wherein said modeling the inter-region movement of the at least two reactants between said different regions based on the defined relationships is performed between a first time step and a second time step in each pair of successive time steps in the sequence of time steps, and wherein defining relationships for inter-region movement of the at least two reactants is selected from the group consisting of defining flux-based molecular movement, defining advection-based molecular movement, defining convection-based molecular movement, defining diffusion-based movement, and combinations thereof, and wherein said modeling the biochemical reaction in each region, said modeling the inter-region movement of the at least two reactants between said different regions, said determining an identification of the product of the biochemical reaction in each region, and said storing the identification of the product of the biochemical reaction in each region are performed by a computer processor.

2. The method of claim 1, wherein at least one reactant of the at least two reactants comprises a molecule.

3. The method of claim 1, wherein defining the biochemical reaction comprises:

defining a plurality of places of a stochastic Petri-net for the biochemical reaction;

defining a plurality of tokens for the biochemical reaction, each token corresponding to a reactant of the at least two reactants and located in one place of the plurality of places of the stochastic Petri-net for the biochemical reaction; and, defining one or more transitions of the stochastic Petri-net, each transition pertaining to the biochemical reaction.

4. The method of claim 3, wherein each transition has one or more of input/output functions, each input/output function having a weight and leading from a place of the plurality of places and leading to a transition of the one or more transitions, each transition being enabled when each place leading to the transition via the input/output function has a number of tokens located therein greater than or equal to the weight of the input/output function.

5. The method of claim 3, wherein at least one place of the plurality of places is an output place having one or more of the input/output functions each leading to the output place and leading from another place or a transition, such that occurrence of each input/output function of the output place results in transfer of tokens from the other place or the transition leading from the input/output function to the output place.

6. The method of claim 3, wherein the method further comprises defining a global marking at a given time for each biochemical reaction as a vector representing a number of tokens in each place at the given time.

7. The method of claim 1, wherein defining the spatial decomposition of the space comprises defining a quad-tree decomposition of the space in accordance with a specified accuracy of said modeling the biochemical reaction in each region.

8. The method of claim 1, wherein defining the spatial decomposition of the space comprises defining the spatial decomposition of the space in accordance with a specified accuracy of said modeling the biochemical reaction in each region.

9. The method of claim 1, wherein modeling the biochemical reactions in each region comprises modeling the biochemical reaction in each region as a spatially homogenous stochastic Petri-net, such that the biochemical reactions in the regions of the plurality of regions interact with one another via the inter-region movement of the at least two reactants.

10. The method of claim 1, said method further comprising performing one or more actions based on a result of said modeling the biochemical reaction in each region.

11. The method of claim 10, wherein said performing one or more actions comprises:

analyzing results of said modeling the biochemical reaction in each region; and/or adjusting the system based on said results.

* * * * *